(12) United States Patent
DeVries

(10) Patent No.: US 10,210,609 B2
(45) Date of Patent: Feb. 19, 2019

(54) INTEGRATED DEEP LEARNING AND CLINICAL IMAGE VIEWING AND REPORTING

(71) Applicant: INTERNATIONAL BUSINESS MACHINES CORPORATION, Armonk, NY (US)

(72) Inventor: Jon DeVries, Chicago, IL (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 206 days.

(21) Appl. No.: 15/258,872

(22) Filed: Sep. 7, 2016

(65) Prior Publication Data

US 2018/0068438 A1     Mar. 8, 2018

(51) Int. Cl.
*G06K 9/66* (2006.01)
*G06T 7/00* (2017.01)
*G06K 9/46* (2006.01)
*A61B 6/03* (2006.01)
*A61B 5/055* (2006.01)
*G06F 17/24* (2006.01)

(52) U.S. Cl.
CPC ............ *G06T 7/0012* (2013.01); *A61B 5/055* (2013.01); *A61B 6/032* (2013.01); *A61B 6/037* (2013.01); *G06F 17/241* (2013.01); *G06K 9/4671* (2013.01); *G06K 9/66* (2013.01)

(58) Field of Classification Search
CPC ......... G06T 7/0012; G06T 2207/10081; G06T 11/006; G06T 7/0081; G06T 2207/10116; G06T 2207/30004; G06T 5/40; G06T 2207/30068; G06T 1/20; G06T 17/20; G06T 1/60; G06T 7/0085; G06T 7/60; A61B 6/032; A61B 5/02007; A61B 5/7264; A61B 5/742; G06F 9/5044; G06F 17/5018; G06F 2217/16; G06K 9/4604; G06K 9/52; G06K 9/6267; G06K 9/66
See application file for complete search history.

(56) References Cited

U.S. PATENT DOCUMENTS

2016/0364631 A1* 12/2016 Reicher ................ G06N 99/005

* cited by examiner

*Primary Examiner* — Duy M Dang
(74) *Attorney, Agent, or Firm* — Foley Hoag LLP; Erik Huestis; Stephen Kenny

(57) ABSTRACT

Integrated deep learning and clinical image viewing and reporting are provided. In some embodiments, a clinical image is received. An annotated image is generated from the clinical image by application of a deep learning system. At least one clinical finding is generated from the clinical image by application of the deep learning system. The annotated image and the at least one clinical finding are provided to a user. A structured report is generated based on the annotated image and the at least one clinical finding.

20 Claims, 3 Drawing Sheets

INTEGRATED DEEP LEARNING AND CLINICAL IMAGE VIEWING AND REPORTING

BACKGROUND

Embodiments of the present invention relate to clinical reporting, and more specifically, to integrated deep learning and clinical image viewing, interpretation, and reporting.

BRIEF SUMMARY

According to one embodiment of the present invention, a method of and computer program product for clinical reporting are provided. A clinical image is received. An annotated image is generated from the clinical image by application of a deep learning system. At least one clinical finding is generated from the clinical image by application of the deep learning system. The annotated image and the at least one clinical finding are provided to a user. A structured report is generated based on the annotated image and the at least one clinical finding.

DETAILED DESCRIPTION

Figure 1:
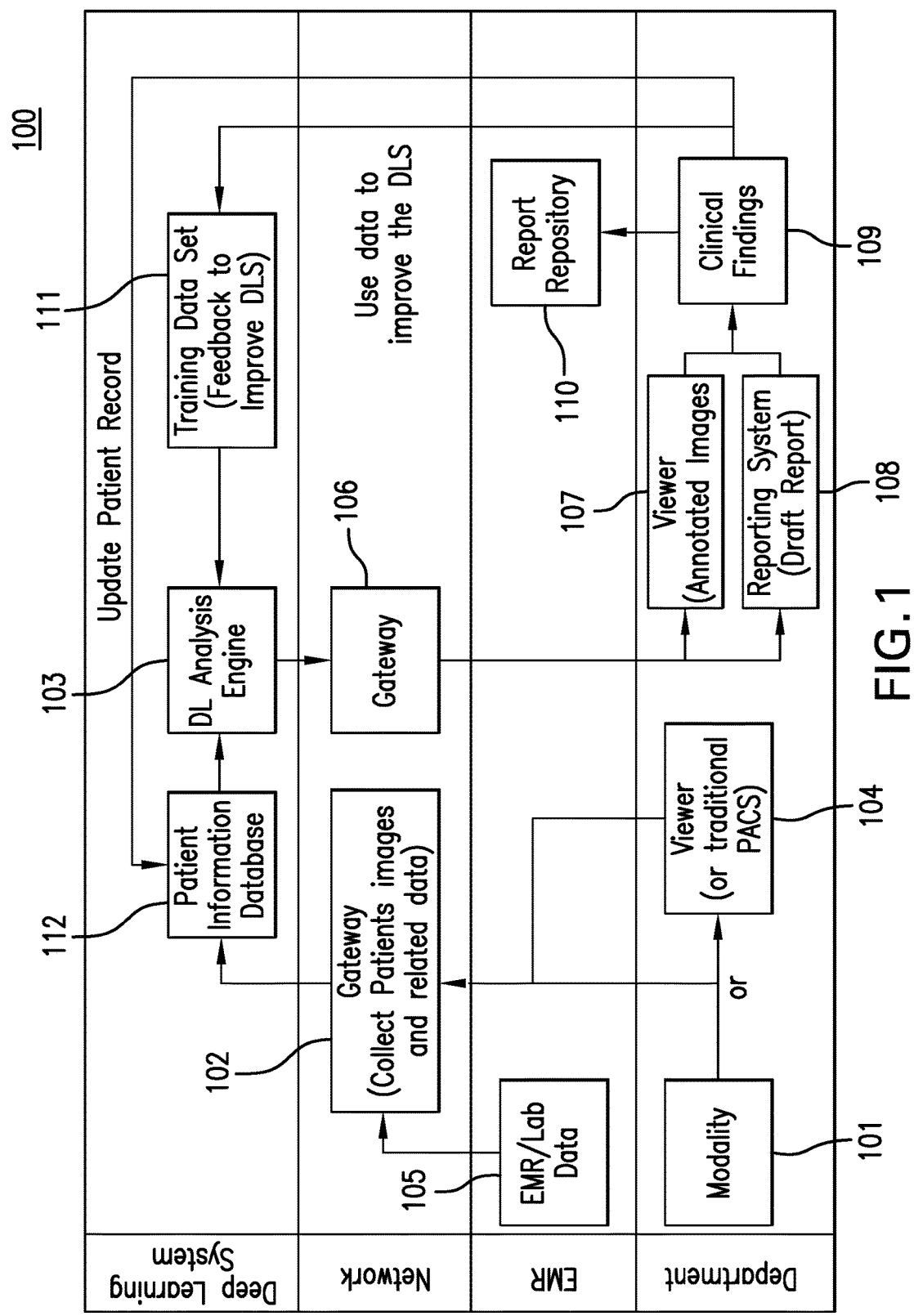
FIG. 1 illustrates an exemplary system and workflow according to embodiments of the present disclosure.

Deep Learning has shown substantial promise in research environments, but has yet to gain traction in real-world clinical settings. Accordingly, the present disclosure provides systems and methods to efficiently, and practically integrate deep learning analysis into a physician's clinical workflow.

According to various embodiments of the present disclosure, systems and methods are provided for injecting the analysis performed by a deep learning system (DLS) into the clinical workflow of image interpretation and reporting. In particular, the deep learning system is integrated during the finding reporting process when using a viewer, such as a PACS or other department specific viewing system. Such processes include sending annotated images and clinic findings from the DLS to the viewing and reporting solutions for the clinical staff to more efficiently, quickly and accurately assess the patients exams in context, generate reports, and deliver their clinical findings to the rest of the enterprise. In this way, the clinical staff can leverage context including a patient's complete medical record and information regarding the individual clinical encounter.

According to various embodiments of the present disclosure, systems and methods are provided for a viewing and reporting system to both deliver clinical findings to the rest of the enterprise and create a feedback loop that sends the updated images and report back to the DLS. In this way, the DLS may be further trained to improve the quality of the analysis for future cases.

To provide for the above features, various embodiments of the present disclosure provide for generation of annotated images by the DLS, which are transmitted back to a customer's viewer. Similarly, the DLS generates one or more clinical finding that is delivered to the reporting system used by the physician. Finally, the reporting system and viewer will send the updated report and annotated images back to the DLS. These three elements allow the DLS to fit into an efficient clinical workflow and enable the DLS to continue to evolve and improve.

In particular, the DLS generated annotated images may include descriptions, labels or measurements. Images may be generated in 2D, 3D, or 4D. Images may be transmitted back to a customer's viewer through a variety of methods.

Generated information may be provided in a variety of forms. For example, in some embodiments, Grey Scale Presentation States (GSPS) objects are inserted back into the original examination image. In some embodiments, one or more XML, file is provided that includes labels, annotations, or location information. Such data can be extracted and used during the review process or while a radiologist edits or creates annotations. In some embodiments, a clinical workflow system queries the DLS via an API to obtain information on the fly. In some embodiments, the generated information is provided as Structured Reports (SR), Secondary Captures (SC), or PDFs. In some embodiments, the generated information is transmitted between the DLS and workflow, viewer, or reporting solutions via Fast Health Interoperability Resources (FHIR).

In various embodiments, the viewer may be an on premise viewer, a hosted viewer, or a cloud based viewer. The viewer ingests the annotated images through at least one of the forms described above, and in some embodiment enables the physician to view and edit the annotations. In some embodiments, the viewer also allows a physician to create new annotations in addition to the ones provided by the DLS. The information passed from the DLS may include labels that are part of the annotations created by the DLS, or added to measurements generated by the physician.

As noted above, in various embodiments the DLS generates a draft of a structured report based on the annotations and measurements that the DLS performs, and deliver this draft report to the reporting system used by the physician. The reporting system may be an on premise reporting system, a hosted reporting system, or a cloud based reporting system. As the physician edits the annotations or creates new ones, the reporting system may be automatically updated. The reporting system may also enable the physician to agree with a reported finding, edit a reported finding, or delete a reported finding. By creating a pre-populated and structured report, a physician will be more efficient and the system is able to report on all of the findings necessary to properly bill for a test.

The reporting system and viewer send the updated report and annotated images back to the DLS to either confirm the analysis performed by the DLS or to re-train the DLS with the updated information.

Systems and methods of the present disclosure are suitable for use in various products, such as: cloud based viewer; Automated Preliminary or "Wet Read" services; PACS systems; systems integrating Universal Worklist and clinically relevant information provided by the DLS; enhanced billing systems driven by the DLS; automated pre-authorization services; or enhanced reporting system that provides clinical findings and diagnosis options, recommended additional tests, or treatment recommendations.

Referring now to FIG. 1, an exemplary system 100 and workflow according to the present disclosure is illustrated in which patient information is transmitted to DLS, routed it back to a customer's viewer and reporting system, and feedback is provided to DLS.

In this exemplary workflow, modality 101 acquires an image. In various embodiments, the modality includes CT (computed tomography), MRI (magnetic resonance imaging), or X-Ray scanners, dermatology cameras, ENT scopes, or other sources of clinical imagery known in the art. In some embodiments, the image is routed directly to gateway 102. In some embodiments, the image is routed directly to the DLS 103. In other embodiments, the image is routed to PACS/Viewer 104 or VNA and then routed to the Gateway 102 or DLS 103.

In some embodiment, EMR 105 or other laboratory systems feeds information to Gateway 102 or DLS 103 to create a complete patient record. The clinical data may be sent to Gateway 102 or DLS 103 via HL7, CDA, or similar transfer mechanisms.

DLS 103 analyzes the information and routes it back through gateway 106. In some embodiments, gateway 102 and 106 are the same entity. In some embodiment, information is routed from DLS 103 directly to viewer 107 and reporting system 108 where they can directly connect to the DLS 103.

In some embodiment, deep learning may be referred to as deep structured learning, hierarchical learning or deep machine learning. In some embodiments, DLS 103 comprises an artificial neural network. Suitable artificial neural networks include but are not limited to a feedforward neural network, a radial basis function network, a self-organizing map, learning vector quantization, a recurrent neural network, a Hopfield network, a Boltzmann machine, an echo state network, long short term memory, a bi-directional recurrent neural network, a hierarchical recurrent neural network, a stochastic neural network, a modular neural network, an associative neural network, a deep neural network, a deep belief network, a convolutional neural networks, a convolutional deep belief network, a large memory storage and retrieval neural network, a deep Boltzmann machine, a deep stacking network, a tensor deep stacking network, a spike and slab restricted Boltzmann machine, a compound hierarchical-deep model, a deep coding network, a multilayer kernel machine, or a deep Q-network.

A user or physician may review, edit, or update information in viewer 107 and amend and finalize the report in reporting system 108. In some embodiments, the report is updated automatically while a physician works with the images. For example, in some embodiments the report is modified on the fly as the annotations made by DLS are edited or as the physician creates new annotations.

Clinical findings 109 are stored in report repository 110. In some embodiments, the report repository is part of an EMR, and maintains a patient's permanent medical record. In some embodiments, clinical findings 109 are also routed back to the DLS 103 as training data set 111 to continuously improve the DLS. In some embodiments, clinical findings 109 are also stored in patient information database 112 as part of a patient's medical record accessible to DLS 103. By adding the information back to the patient's medical record in DLS, DLS has a longitudinal record for the patient. Having a patient's prior information allows DLS to analyze the patients' next visit. In some embodiments, database 112 is replaced by another data store, such as a flat file, a NoSQL store, an XML file, or other storage known in the art.

As described further above, the present disclosure provides for a viewer and reporting system to ingest data so that it can be edited, updated, and verified. In some embodiments, where they cannot accept this type of data, variant data is sent, including static information such as secondary capture images, PDF reports, or a CDA document.

In some embodiments, the gateway functionality is built into an EMR, modality, or Viewer/PACS/VNA. As noted above, a dedicated gateway is not mandatory if the component systems support gateway-like functionality.

Figure 2:
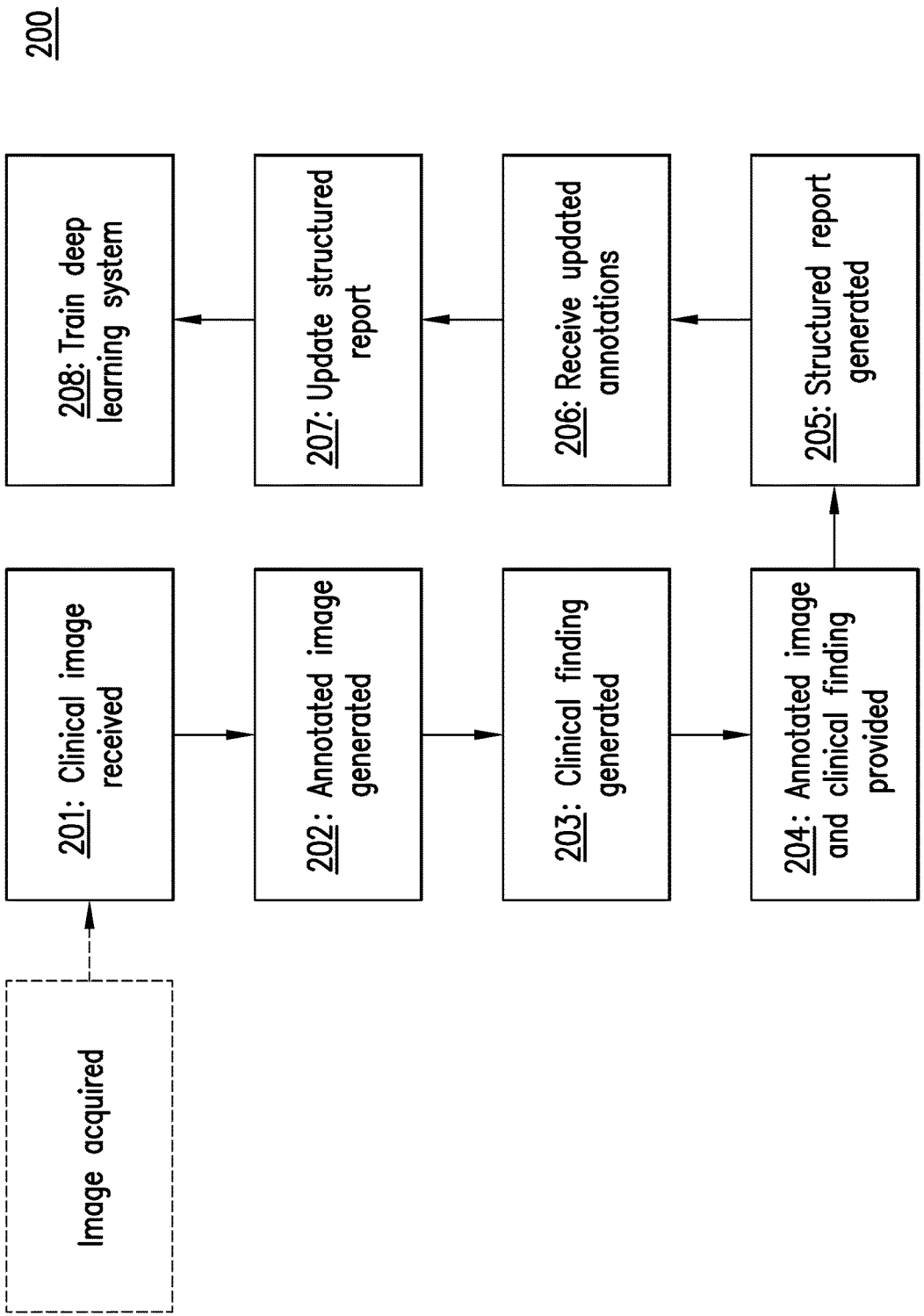
FIG. 2 illustrates an exemplary method according to embodiments of the present disclosure.

With reference now to FIG. 2, an exemplary method 200 according to embodiments of the present disclosure is illustrated. At 201, a clinical image is received. In some embodiments, the image is received after acquisition. In some embodiments, clinical data associated with the clinical image is also received. At 202, an annotated image is generated from the clinical image by application of a deep learning system. At 203, at least one clinical finding is generated based on the clinical image by application of the deep learning system. In some embodiments where clinical data is associated with the clinical image, the at least one clinical finding is based on the clinical data associated with the clinical image. In some embodiments, the deep learning system performs one or more analyses on the image and clinical data. Exemplary analyses include: identifying, localizing, and annotating abnormalities found in the image; generating clinical findings based on the image and the clinical data; generating a differential diagnosis or similar clinical decision support guidance; or generating treatment recommendations.

At 204, the annotated image and the at least one clinical finding are provided to a user. In some embodiments, this information is transferred to a viewer and/or reporting system that provides the annotated image and clinical finding(s) to a user. In some embodiments, the user accesses the image and finding through such systems. In some embodiments, this information is transmitted back to a clinical workflow solution, such as a Picture Archive and Communication System (PACS), Electronic Health Record (EHR) system, worklist manager, or viewer. Such solutions may be used by users including radiologists, cardiologists, physicians, technologists, and nurses. The user may access this information via the viewer, reporting, or workflow system to care for a patient. In some embodiments, the user reviews the annotated image and the at least one clinical finding, and accepts, edits, or rejects the analysis of the deep learning system.

At 205, a structured report is generated based on the annotated image and the at least one clinical finding. In some embodiments, the structured report is generated by a fully automated report generation tool. In other embodiments, the user participates in the generation and editing of the report. In some embodiments, the user uses a viewer and/or reporting solution to view and edit the annotated images and clinical findings and generate a report. At 206, a plurality of updated annotations to the annotated image are received from the user. In some embodiments, a plurality of updates to the at least one clinical finding are also received from the user. At 207, the structured report is updated based on the plurality of updated annotations. At 208, the deep learning system is trained based on the plurality of updated annotations. In this manner, the deep learning system learns from user insight and actions.

Figure 3:
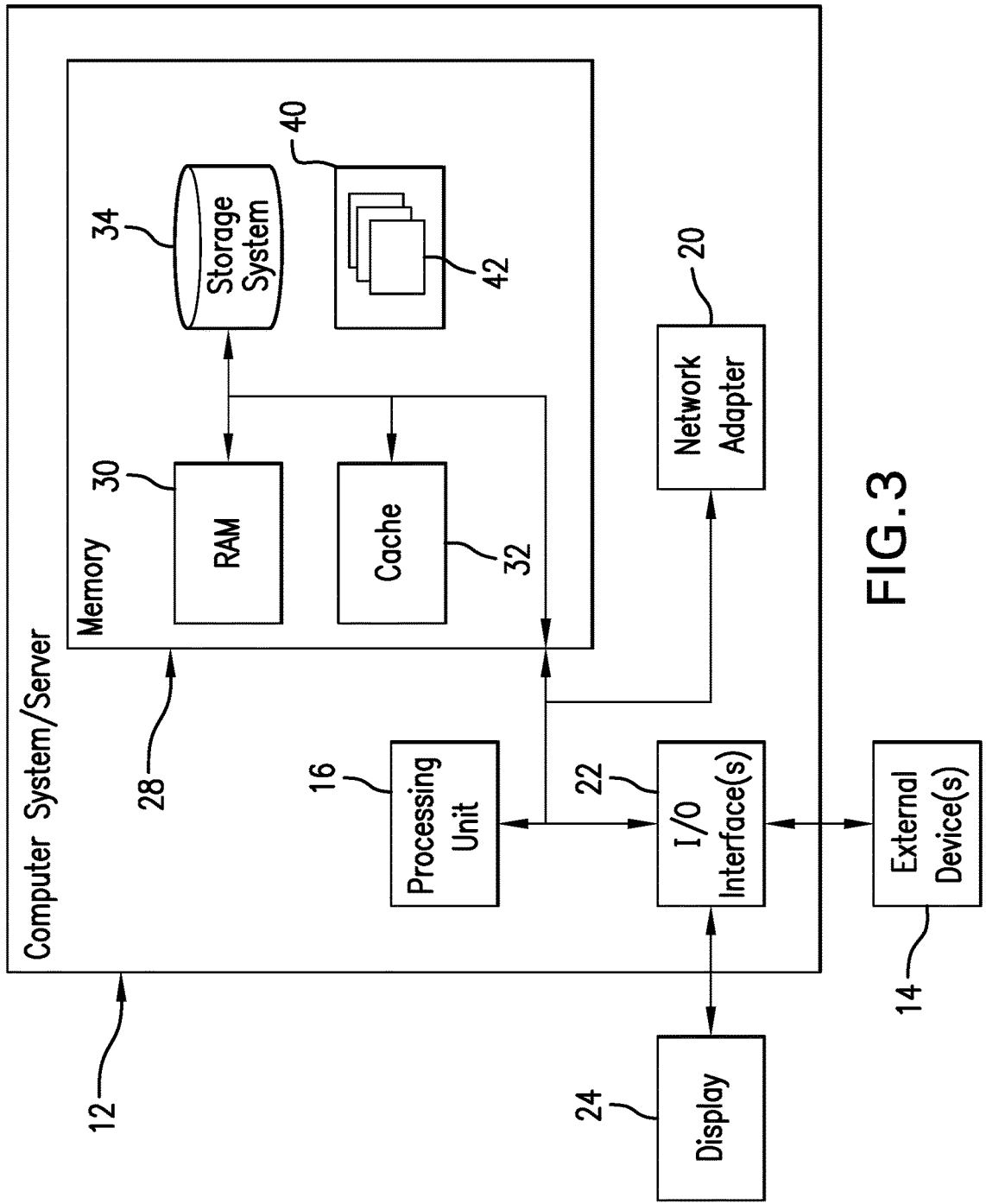
FIG. 3 depicts a computing node according to embodiments of the present disclosure.

Referring now to FIG. 3, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   receiving a clinical image;
   generating an annotated image from the clinical image by application of a deep learning system;
   generating at least one clinical finding based on the clinical image by application of the deep learning system;
   providing the annotated image and the at least one clinical finding to a user;
   generating a structured report based on the annotated image and the at least one clinical finding.

2. The method of claim 1, further comprising:
   receiving from the user a plurality of updated annotations to the annotated image;
   training the deep learning system based on the plurality of updated annotations.

3. The method of claim 1, further comprising:
   receiving clinical data associated with the clinical image, and wherein the at least one clinical finding is based on the clinical data associated with the clinical image.

4. The method of claim 1, wherein the clinical image comprises computed tomography, magnetic resonance imagery, ultrasound imagery, white light imaging, positron emission tomography imagery, angiography, single-photon emission computed tomography, or X-ray imagery.

5. The method of claim 1, further comprising acquiring the clinical image from a medical imaging modality.

6. The method of claim 1, wherein the deep learning system comprises an artificial neural network.

7. The method of claim 1, wherein providing the annotated image to the user comprises:

providing an annotation layer reflecting features of interest.

8. The method of claim 7, wherein the annotation layer comprises grey scale presentation states objects, structured report objects, or secondary capture objects.

9. The method of claim 1, wherein providing the annotated image comprises displaying the annotated image through a viewer.

10. The method of claim 1, wherein providing the annotated image and the at least one clinical finding to the user comprises routing through a gateway.

11. The method of claim 1, further comprising:
receiving from the user a plurality of updates to the at least one clinical finding;
updating the structured report based on the plurality of updates to the at least one clinical finding.

12. The method of claim 11, further comprising:
training the deep learning system based on the plurality of updates to the at least one clinical finding.

13. The method of claim 11, further comprising:
storing the updated structured report in a data store.

14. A computer program product for clinical reporting, the computer program product comprising a computer readable storage medium having program instructions embodied therewith, the program instructions executable by a processor to cause the processor to perform a method comprising:
receiving a clinical image;
generating an annotated image from the clinical image by application of a deep learning system;
generating at least one clinical finding based on the clinical image by application of the deep learning system;
providing the annotated image and the at least one clinical finding to a user;
generating a structured report based on the annotated image and the at least one clinical finding.

15. The computer program product of claim 14, the method further comprising:
receiving from the user a plurality of updated annotations to the annotated image;
updating the structured report based on the plurality of updated annotations;
training the deep learning system based on the plurality of updated annotations.

16. The computer program product of claim 14, the method further comprising:
receiving clinical data associated with the clinical image, and wherein the at least one clinical finding is based on the clinical data associated with the clinical image.

17. The computer program product of claim 14, the method further comprising acquiring the clinical image from a medical imaging modality.

18. The computer program product of claim 14, wherein providing the annotated image to the user comprises:
providing an annotation layer reflecting features of interest.

19. The computer program product of claim 14, the method further comprising:
receiving from the user a plurality of updates to the at least one clinical finding;
updating the structured report based on the plurality of updates to the at least one clinical finding.

20. The computer program product of claim 19, the method further comprising:
training the deep learning system based on the plurality of updates to the at least one clinical finding.

* * * * *